(12) United States Patent
Kaplan et al.

(10) Patent No.: US 8,530,619 B2
(45) Date of Patent: Sep. 10, 2013

(54) IDENTIFICATION OF THE HEPCIDIN BINDING SITE ON FERROPORTIN

(75) Inventors: Jerry Kaplan, Salt Lake City, UT (US); Diane M. Ward, Salt Lake City, UT (US); Ivana De Domenico, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 102 days.

(21) Appl. No.: 12/734,061

(22) PCT Filed: Oct. 27, 2008

(86) PCT No.: PCT/US2008/012231
§ 371 (c)(1), (2), (4) Date: Apr. 8, 2010

(87) PCT Pub. No.: WO2009/055078
PCT Pub. Date: Apr. 30, 2009

(65) Prior Publication Data
US 2010/0292147 A1    Nov. 18, 2010

Related U.S. Application Data

(60) Provisional application No. 61/000,584, filed on Oct. 26, 2007.

(51) Int. Cl.
*C07K 14/46* (2006.01)

(52) U.S. Cl.
USPC .......... 530/300; 530/324; 530/325; 530/810; 530/811; 530/812

(58) Field of Classification Search
None
See application file for complete search history.

(56) References Cited

U.S. PATENT DOCUMENTS

| | | | |
|---|---|---|---|
| 4,983,524 A | 1/1991 | Fujikawa et al. | |
| 5,824,478 A * | 10/1998 | Muller | 435/6.12 |
| 7,169,758 B2 | 1/2007 | Nicolas et al. | |
| 7,749,713 B2 * | 7/2010 | Kulaksiz et al. | 435/7.1 |
| 2006/0019339 A1 | 1/2006 | Lauth et al. | |
| 2006/0281130 A1 | 12/2006 | Bock et al. | |
| 2007/0224186 A1 | 9/2007 | Kulaksiz et al. | |

FOREIGN PATENT DOCUMENTS
EP    1 262 187    12/2002

OTHER PUBLICATIONS

Liu et al., Blood Cells, Molecules, and Diseases, 35(1):33-46, 2005.*
De Domenico, I. et al., The Hepcidin-Binding Site on Ferroportin Is Evolutionarily Conserved. *Cell Metabolism*. Aug. 6, 2008, No. 8, pp. 146-156.
Park, C. H. et al., Hepcidin, a Urinary Antimicrobial Peptide Synthesized in the Liver. *The Journal of Biological Chemistry*. Mar. 16, 2001, vol. 276, No. 11, pp. 7806-7810.
Kulaksiz, H. et al., Pro-hepcidin: expression and cell specific localisation in the liver and its regulation in hereditary haemochromatosis, chronic renal insufficiency, and renal anaemia. *J. Gut*. Sep. 2003, vol. 53, pp. 735-743.
Bloustine, J. et al., Measurements of Protein-Protein Interactions by Size Exclusion Chromatography. *Biophysical Journal*. Oct. 2003, vol. 85, pp. 2619-2623.
Papanikolaou, G. et al., Hepcidin in iron overload disorders. *Blood*. May 15, 2005, vol. 105, No. 10, pp. 4103-4105.
Détivaud, L. et al., Hepcidin levels in humans are correlated with hepatic iron stores, hemoglobin levels, and hepatic function, *Blood*. Jul. 15, 2005, vol. 106, No. 2, pp. 746-748.
Kulaksiz, H. et al., The iron-regulatory peptide hormone hepcidin: expression and cellular localization in the mammalian kidney. *Journal of Endocrinology*. 2005, vol. 184, pp. 361-370.
Rivera, S. et al., Synthetic hepcidin causes rapid dose-dependent hypoferremia and is concentrated in ferroportin-containing organs. *Blood*. Sep. 15, 2005, vol. 106, No. 6, pp. 2196-2199.
IBL Instructions for Use., Hepcidin Prohormone ELISA (RE54051): Enzyme immunoassays for the quantitative determination of Pro-Hepcidin in human serum. Version 10.0 / 2005-09, pp. 1-7.
Nemeth, E. et al., The N-terminus of hepcidin is essential for its interaction with ferroportin: structure-function study. *Blood*. Jan. 1, 2006, vol. 107, No. 1, pp. 328-333.
Vokurka, M. Et al., Hepcidin mRNA Levels in Mouse Liver Respond to Inhibition of Erythropoiesis. *Physiological Research*. 2006, vol. 55, pp. 667-674.
Sheikh, N. et al., Hepcidin and hemojuvelin gene expression in rat liver damage: in vivo and in vitro studies. *Gastrointestinal and Liver Physiology*. Mar. 30, 2006, vol. 291, pp. G482-G490.
Tomosugi, N. et al. Detection of serum hepcidin in renal failure and inflammation by using ProteinChip System®. *Blood*. Apr. 26, 2006, vol. 10, pp. 1-20.
Oğuz, A. et al., Hepcidin is not a marker of chronic inflammation in atherosclerosis. *Anadolu Kardiyol Derg*. 2006, vol. 66, pp. 239-242.
Fujita, N. et al., Hepcidin Expression in the Liver: Relatively Low Level in Patients with Chronic Hepatitis C. *Mol Med*. Jan. 2007, vol. 13, Nos. 1-2, pp. 97-104.
De Domenico, I. et al., Hpcidin regulation: ironing out the details. *The Journal of Clinical Investigation*. Jul. 2007, vol. 117, No. 7, pp. 1755-1758.
De Domenico et al., "Iron overload due to mutations in ferroportin," Haematologica, vol. 91, No. 1, pp. 92-95 (2006).
Drakesmith, et al., "Resistance to hepcidin is conferred by hemochromatosis-associated mutations of ferroportin," *Blood*, vol. 106, No. 3, pp. 1092-1097, Aug. 1, 2005.
Wallace et al., "A novel mutation in ferroportin implicated in iron overload," Journal of Hepatology, vol. 46, No. 5, pp. 921-926 (2007).

* cited by examiner

*Primary Examiner* — Marianne P Allen
(74) *Attorney, Agent, or Firm* — Michael Best & Friedrich LLP

(57) ABSTRACT

The invention relates to materials and procedures for the use of the hepcidin binding domain (HBD) on ferroportin. A 20 amino acid peptide of the HBD was synthesized and shown to recapitulate the characteristics and specificity of hepcidin binding to cell surface ferroportin. The affinity of hepcidin for the HBD peptide permits a rapid, sensitive assay of hepcidin in biological fluids.

8 Claims, 9 Drawing Sheets

IDENTIFICATION OF THE HEPCIDIN BINDING SITE ON FERROPORTIN

CROSS-REFERENCE TO RELATED APPLICATIONS

This patent application is a national stage filing under 35 U.S.C. 371 of International Patent Application No. PCT/US2008/012231, filed Oct. 27, 2008, which claims the benefit of priority to U.S. Provisional Patent Application No. 61/000,584, filed Oct. 26, 2007, which are incorporated herein by reference in their entireties. Priority to each application is hereby claimed

STATEMENT REGARDING FEDERALLY SPONSORED RESEARCH OR DEVELOPMENT

This invention was made with Government support under Grant DK 070947, awarded by the National Institutes of Health. The U.S. Government has certain rights to this invention.

TECHNICAL FIELD

The invention relates generally to biotechnology and more particularly to the identification of the hepcidin binding site on ferroportin and its therapeutic and analytical use, for example, measuring hepcidin levels.

BACKGROUND

The following discussion of the background of the invention is provided to aid the reader in understanding the invention and is not an admission that anything herein describes or constitutes prior art.

Systemic iron homeostasis is dependent on the expression of the liver peptide hormone hepcidin and its interaction with the cell surface iron transporter ferroportin (Fpn) (for review see (1)). Fpn exports iron from cells to the plasma and is responsible for iron absorption from the intestine, recycling of erythrocyte iron by macrophages and maternal delivery of iron to the fetus. Transcription of hepcidin in hepatocytes is regulated by the levels of cytokines, hypoxia and iron stores. Once secreted, hepcidin binds to Fpn and induces its internalization and degradation (2). Binding of hepcidin to Fpn leads to the phosphorylation of either of two adjacent tyrosines in a cytosolic domain resulting in the internalization of phosphorylated Fpn by coated pits (3). Mutations in Fpn that prevent hepcidin binding to Fpn or Fpn phosphorylation subsequent to hepcidin binding, and Fpn/hepcidin internalization, result in hepatic iron overload disease (4). The low level of hepcidin in plasma and the lack of useful anti-hepcidin antibodies have made assay of plasma hepcidin levels problematic, although it may be assayable by mass spectroscopy.

Hepcidin deficiency or alterations in ferroportin result in dysregulated iron absorption, tissue maldistribution of iron, and iron overload. For example, hepcidin deficiency has been reported in hereditary hemochromatosis and is attributed to mutations in HFE, transferrin receptor 2, hemojuvelin, and the hepcidin gene itself. Hepcidin levels have been found to be suppressed in patients with thalassemia syndromes, congenital dyserythropoietic anemia type 1, juvenile hemochromatosis, and hereditary hemochromatosis (type 1 hemochromatosis). Hepcidin levels have also been found to be elevated in patients with hemochromatosis type 4 (ferroportin disease) and anemia of inflammation. As a result of hepcidin's critical role in iron homeostasis, measurement of hepcidin levels is important in the diagnosis and treatment of iron homeostasis diseases and disorders.

Hence, there is a need in the art for a reliable and rapid diagnostic, prognostic and/or predictive method that can accurately measure hepcidin levels in a biological fluid.

SUMMARY OF THE INVENTION

The invention relates to diagnostic, prognostic and/or predictive methods comprising measuring hepcidin levels in a subject using a Hepcidin Binding Domain (HBD), synthesized based on the hepcidin binding site on ferroportin, and using or correlating those measurements to diagnose, prognose or predict an iron homeostasis disease or disorder.

The invention also relates to a method of screening a compound for modulation of hepcidin or hepcidin activity. In another exemplary embodiment, the invention relates to a method of screening a compound for modulation of liver cell production of hepcidin.

The invention also relates to the use of the hepcidin binding domain of ferroportin (HBD) for the treatment of an iron homeostasis disease or disorder. In an exemplary embodiment the HBD comprises a forty amino acid peptide, a thirty five amino acid peptide, a thirty amino acid peptide, a twenty five amino acid peptide, or a twenty four amino acid peptide having the sequence FDCITTGYAYTQGLSGSILS (SEQ ID NO:1) or derivatives thereof. In another exemplary embodiment, the HBD is modified by the addition of hydrophilic amino acids selected from the group consisting of arginine (Arg), aspartic acid (Asp), glutamic acid (Glu), glutamine (Gln), lysine (Lys), histidine (His), serine (Ser), threonine (Thr), and combinations thereof.

The invention also relates to the manufacture of medicaments comprising the HBD, which medicaments are useful in preventing and/or treating iron homeostasis diseases or disorders, particularly diseases or disorders characterized by elevated levels of hepcidin or deficient intestinal absorption of iron, such as chronic renal insufficiency, anemia of inflammation and anemia of aging.

The invention has particular relevance to iron homeostasis diseases or disorders that are typically characterized by aberrant or otherwise inappropriate iron absorption, tissue maldistribution of iron, and iron overload, which diseases and disorders include, but are not limited to: iron deficiency anemia; hemosiderosis, hemochromatosis, secondary hemochromatosis, juvenile hemochromatosis, aceruloplasminemia, hypotransferrinemia, atransferrinemia, liver diseases (for example, alcoholic liver diseases, nonalcoholic steatohepatitis, and chronic hepatitis B and C infections), chronic inflammatory diseases, sideroblastic anemia, thalassemia, leukemia, polyglobulie, macrocytic, microcytic, normocytic anemia, anemia with reticulocytosis, hemolytic anemia, immunologic diseases and tumors (for example, carcinoma, sarcoma, or lymphoma, which may result in non-physiologic hepcidin concentrations), Alzheimer's disease and Wilson's disease.

BRIEF DESCRIPTION OF THE DRAWINGS

FIG. 1A shows the results of HEK293TFpn-GFP cells incubated with or without hepcidin (1 µg/ml) or with hepcidin that had been pre-incubated either with HBD, scrambled-HBD or HBD with the C326Y mutation. The HBD peptides and hepcidin were mixed at an equal molar ratio for two hours at 37° C. and then added to cells for one or 24 hours. Fpn internalization at one hour was analyzed by epifluorescence (upper panel) and the percentage of cells showing internalized Fpn-GFP at one and 24 hours was quantified (lower panel). The data represent the standard error of the mean from analyzing over 10 fields (20-30 cells) per sample. FIG. 1B illustrates HBD inhibition of Fpn-GFP internalization. Fpn-GFP expressing cells were incubated with hepcidin, hepcidin preincubated with HBD at 37° C. or hepcidin preincubated with HBD at 4° C. Fpn-GFP internalization at one (black bars) and 24 (grey bars) hours was quantified. The percentage of cells with internalized Fpn is shown. FIG. 1C illustrates that $^{125}$I-hepcidin binds to HBD similarly to unlabeled hepcidin. $^{125}$I-hepcidin was preincubated with HBD at 37° C. or 4° C. for one hour and then the mixture added to cells for one hour (black bars) or twenty-four hours (grey bars). The data are expressed as in FIG. 1B. FIG. 1D illustrates the fact that binding of hepcidin to HBD is reversible by low temperature. In the left panel the samples were treated as in FIG. 1C. In the right panel, the sample was incubated at 37° C. and was placed at 4° C. for four hours. The mixture was then incubated with cells at 37° C. and the internalization of Fpn-GFP was determined after one (black bars) or twenty four hours (grey bars).

In FIG. 2A peptides (HBD, scrambled-HBD or mutant (C326Y HBD) were conjugated to beads and $^{125}$I-hepcidin was added to the bead-immobilized peptides (I-HBD) for 18 hours at 37° C. (black bars) or 4° C. (grey bars). The beads were washed and the amount of $^{125}$I-hepcidin bound to the I-HBD was determined. In FIG. 2B a sub saturating concentration of $^{125}$I-hepcidin (0.6 µg/ml) was incubated with I-HBD for 18 hours at 37° C. in the presence or absence of known concentrations of either hepcidin 25 (Hep 25-open circles) or hepcidin 25 synthesized with a tyrosine substitution at position M21 (Y-Hep 25) and the amount of radioactivity bound to the I-HBD determined. In FIG. 2C sub saturating levels of $^{125}$I-hepcidin were incubated with I-HBD at different temperatures. The data shows that binding of hepcidin to HBD is reduced at temperatures below 15° C.

In FIG. 3A $^{125}$I-hepcidin was added to I-HBD and a complex was allowed to form at 37° C. The I-HBD/$^{125}$I-hepcidin complex was washed and then incubated with an excess of non-radioactive hepcidin. The samples were then incubated at 37° C. (closed circle) or 4° C. (open circle) for the specified times and the amount of radioactivity remaining bound to the I-HBD was determined. The data are expressed as radioactivity at each time point relative to the amount bound at time zero. In FIG. 3B the $^{125}$I-hepcidin/1-HBD complex was allowed to form at 37° C., the complex was then washed and incubated with the indicated concentration of NEM and the amount of bound radioactivity was determined after a four-hour incubation (closed circles). I-HBD alone was also incubated with the specified concentrations of NEM for 2 hours. The I-HBD beads were washed and then $^{125}$I-hepcidin was added at 37° C. and the amount of bound radioactivity was determined after a four-hour incubation (open circles).

In FIG. 4A, hepcidin (Hep), HBD or an equal molar mixture of HBD and hepcidin were analyzed by circular dichroism (CD) at 37° C. and 4° C. The insert shows the effect of temperature on the CD spectrum of hepcidin measured at 210 nm. FIG. 4B illustrates the CD spectrum of hepcidin 20 (Hep20) (100 µM) measured at different temperatures. In FIG. 4C, $^{125}$I-hepcidin was applied to G-25 columns that were equilibrated and run at 25° C. (black bars) or 4° C. (grey bars) and the amount of radioactivity in fractions was determined. The arrows represent the elution of molecular weight standards, insulin (5808 Da) and DBI (2150 Da). The elution of the standards was not affected by temperature.

In FIG. 5A, different concentrations of serum were incubated with a known amount of $^{125}$I-hepcidin and I-HBD for 18 hours at 37° C. The beads were washed and radioactivity bound to the beads was determined. A standard curve was determined by incubating known amounts of hepcidin with $^{125}$I-hepcidin and HBD-beads. In FIG. 5B, sera was obtained from wild type mice (C57/Bl6) or from mice that were homozygous for a targeted gene deletion in HFE or homozygous or heterozygous for a targeted gene deletion in the HAMP gene. Samples of sera (25 µL) were incubated with I-HBD and known concentration of $^{125}$I-hepcidin for 18 hours at 37° C. The beads were washed and the amount of radioactivity was determined. Serum hepcidin levels were calculated relative to a standard curve. In FIG. 5C, C3H mice were injected intraperitoneally with LPS. Sera was obtained from the mice 10 hours later and the hepcidin concentration was determined as described in FIG. 5A. In FIG. 5D hepcidin levels were measured in different strains of mice. In FIG. 5E human sera was collected from a control individual and from a patient diagnosed with juvenile hemochromatosis due to mutations in HJV. Hepcidin levels were determined as in FIG. 5A. The serum iron (SI), transferrin binding capacity (TIBC) and transferrin saturation was calculated as described herein. Each sample was analyzed in triplicate and the error bars represent the standard deviation In FIG. 6, hepcidin levels were measured in serum samples from stored control humans of different ages and gender. Each bar represents duplicate measurement of five different individuals. The error of different measurements on the same patient is less than 0.5% (data not shown).

FIG. 8A illustrates joint movement measurements conducted on control mice and mice infected with Borrelia burgdorferi, the organism that is the predominant cause of Lyme disease, to determine the severity of the disease at four weeks post infection. In FIG. 8B, hepcidin levels in sera samples in the control and infected mice was determined using HBD-beads in coded samples, as described fully in Example II. In FIG. 8C, Interleukin-6 (IL-6) serum levels were also analyzed as an inflammatory marker in the control mice and infected mice at weekly stages post infection. The IL-6 serum level assays were conducted by known techniques. In FIG. 8D, hepcidin serum levels were measured in four human patients, one being a non-infected human and three being humans known to be infected with Lyme disease. Hepcidin levels in the human patients were determined using the HBD-bead assay described in Example II, herein, using transferrin saturation and serum iron as parameters involved in iron metabolism and correlated to hepcidin. FIG. 8E shows the inverse relationship between hepcidin levels and transferrin saturation levels in the patients.

DETAILED DESCRIPTION OF THE INVENTION

Figure 1A:
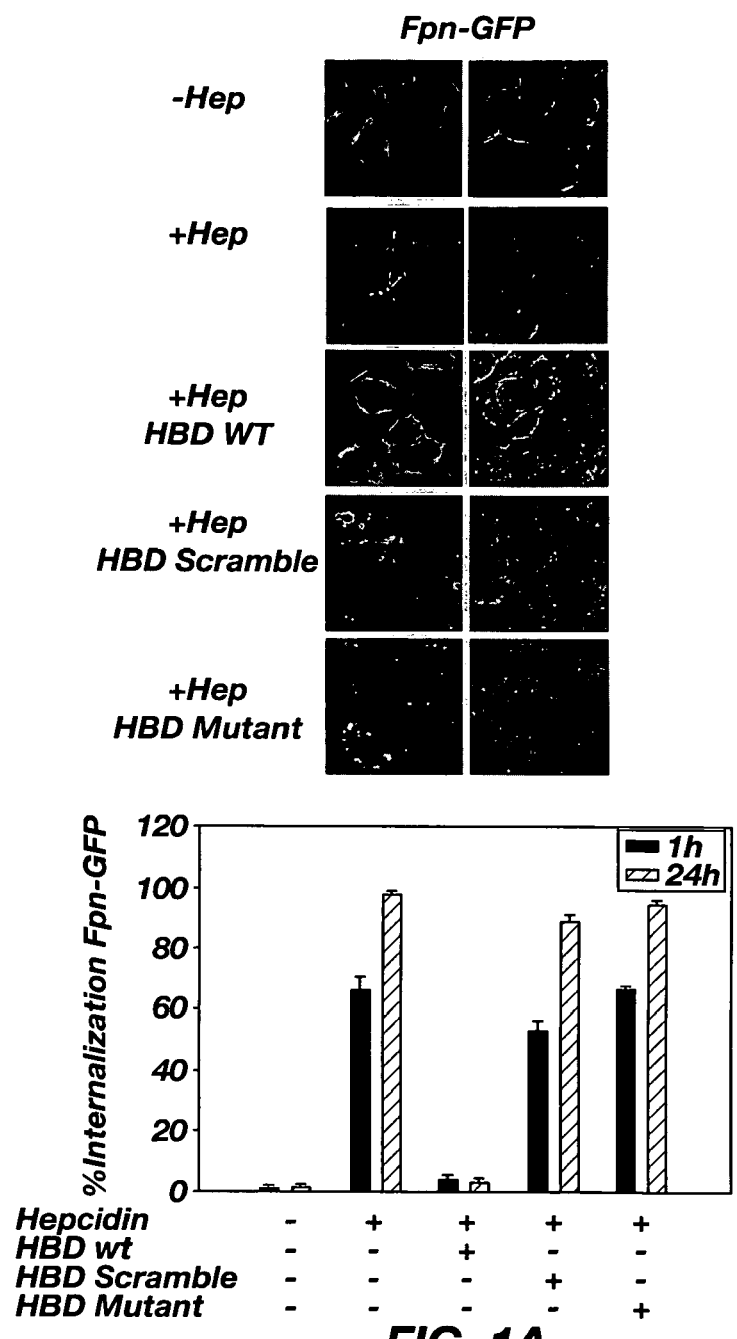
FIGS. 1A-D illustrate inhibition of hepcidin-mediated Fpn internalization by HBD.

As used herein, "about" means reasonably close to, or approximately, a little more or less than the stated number or amount.

As used herein, "blood" means whole blood or any fraction thereof, for example plasma, platelets, and a plasma concentrate.

As used herein, "detectable moiety" or a "label" refers to a compound or composition detectable by spectroscopic, photochemical, biochemical, immunochemical, or chemical means. For example, useful labels include, but are not limited to, $^{32}P$, $^{35}S$, $^{3}H$, $^{125}I$, fluorescent dyes, electron-dense reagents, enzymes, biotin-streptavadin, digoxigenin, haptens and proteins.

As used herein, "disease prediction," "prediction" or similar terms, means to predict the probable onset of a disease before it occurs.

As used herein, "diagnosis" or "diagnostic" means a prediction of the type of disease or condition from a set of marker values, such as hepcidin levels, and/or patient symptoms.

As used herein, "hepcidin" means any mammalian hepcidin or pro-hepcidin (also called LEAP (liver-expressed antimicrobial peptide)) polypeptide such as those that can be found in GenBank™, including, but not limited to, accession numbers NP066998 (protein), AAH20612 (protein), AAG23966 (cDNA) and P81172 (hepcidin precursor). The hepcidin gene encodes an 84-amino acid prepropeptide with a typical signal sequence and a consensus cleavage site for a prohormone convertase that generates the mature bioactive 25-amino acid form found in plasma and urine. The term "hepcidin" also includes purified hepcidin proteins, which may or may not be modified or deliberately engineered (see U.S. Pat. No. 7,169,758). For example, modifications in a hepcidin peptide or DNA sequences can be made by those skilled in the art using known techniques and include, but are not limited to, amino acid alteration, substitution, replacement, insertion or deletion. Preferably, such alteration, substitution, replacement, insertion or deletion retains the desired activity of the hepcidin protein.

As used herein, "hepcidin binding domain" or "HBD" means a peptide comprising the sequence FDCITTGYAY-TQGLSGSILS (SEQ ID NO:1), as well as peptidomimetics and derivatives that may include amino acid alteration, substitution, replacement, insertion or deletion, wherein such alteration, substitution, replacement, insertion or deletion retains the ability to bind to hepcidin.

As used herein, "iron homeostasis disease or disorder" includes, but is not limited to, iron deficiency anemia; haemosiderosis, hereditary haemochromatosis, secondary haemochromatosis, aceruloplasminemia, hypotransferrinemia, atransferrinemia, liver diseases (for example, alcoholic liver diseases, nonalcoholic steatohepatitis, chronic renal insufficiency, renal anaemia, and chronic hepatitis B and C infections), chronic inflammatory diseases, sideroblastic anemia, thalassemia, leukemia, polyglobulie, macrocytic, microcytic, normocytic anemia, anemia with reticulocytosis, hemolytic anemia, immunologic diseases and tumors (for example, carcinoma, sarcoma, or lymphoma, which result in non-physiologic hepcidin concentrations), Alzheimer's disease and/or Wilson's disease.

As used herein, "Peptide," "Polypeptide" and "Protein" include polymers of two or more amino acids of any length, and includes post-translational-modification, without restriction on length. No distinction, based on length, is intended between a peptide, a polypeptide or a protein.

As used herein, "prognosis" or "prognostic", means to predict disease progression at a future point in time from one or more indicator values.

As used herein, "sample" means any sample of biological material derived from a subject, such as, but not limited to, blood, plasma, mucus, biopsy specimens and fluid, which has been removed from the body of the subject. The sample which is tested according to the method of the invention may be tested directly or indirectly and may require some form of treatment prior to testing. For example, a blood sample may require one or more separation steps prior to testing. Further, to the extent that the biological sample is not in liquid form, (for example it may be a solid, semi-solid or a dehydrated sample) it may require the addition of a reagent, such as a buffer, to mobilize the sample.

As used herein, "subject" means a mammal, including, but not limited to, a human, horse, bovine, dog, or cat.

As used herein, "treating" or "treatment" does not require a complete cure. It means that the symptoms of the underlying disease are at least reduced, and/or that one or more of the underlying cellular, physiological, or biochemical causes or mechanisms causing the symptoms are reduced and/or eliminated. It is understood that reduced, as used in this context, means relative to the state of the disease, including the molecular state of the disease, not just the physiological state of the disease.

As used herein, "comprising," "including," "containing," "characterized by," and grammatical equivalents thereof are inclusive or open-ended terms that do not exclude additional, unrecited elements or method steps, but also includes the more restrictive terms "consisting of" and "consisting essentially of."

As used herein and in the appended claims, the singular forms, for example, "a", "an", and "the," include the plural, unless the context clearly dictates otherwise. For example, reference to "a hepcidin binding domain peptide" includes a plurality of such hepcidin binding domain peptides.

Plasma hepcidin concentration is elevated in body iron excess and by inflammatory stimuli, and is lowered in erythroid iron demand, hypoxia and most types of hereditary haemochromatosis. Particularly in the case of hereditary haemochromatosis, diagnosis of the disease before irreversible tissue damage arises is of critical importance. Furthermore, it is desirable to differentiate between ongoing iron accumulation and increasingly prevalent disorders with elevated serum ferritin such as the metabolic syndrome. As a result, an accurate test for hepcidin is needed. Recently, the physiological concentration of pro-hepcidin has been measured by ELISA assay (e.g., the Hepcidin Prohormone ELISA kit available from Immuno-Biological Laboratories); however, this test has proven to be problematic. For example, the test has yielded widely varying concentrations in healthy volunteers and subjects suffering from a number of an iron homeostasis diseases or disorders. For example, U.S. Patent Publication 20040096990 states that the physiological range is 200-260 ng/mL, Kulaksiz et al. (2003) report a pro-hepcidin serum concentration of 106.2 ng/ml in healthy volunteers, Sheikh et al. report a finding of about 242 ng/ml in healthy subjects, and Kulaksiz et al. (2005) report a finding of 104.2 ng/ml in healthy subjects. Therefore, due to problems with antibody production and the ability to only measure prohepcidin, it is apparent that the antibody based ELISA assay for prohepcidin needs to be improved.

In contrast to the antibody based ELISA assay which is dependent upon antibody recognition, the present invention provides a method of measuring hepcidin levels that is independent of an antibody directed to hepcidin. The invention uses a peptide base on hepcidin's native binding partner, which provides a significant improvement in the ability to measure bioactive hepcidin levels that can then be correlated with a disease state to provide a diagnosis, prognosis and/or prediction of a disease or disorder.

In an exemplary embodiment, the invention provides an assay for measuring the amount of hepcidin in a sample of tissue, blood or body fluid from a patient, where the detection and/or quantitative measurement of hepcidin protein in the sample is useful in diagnosing, confirming a clinical diagnosis, or following the course of iron homeostasis diseases. The invention is also useful in monitoring the disease during and subsequent to a period of treatment with agents that are being tested for their ability to stabilize, decrease or prevent the occurrence of such diseases.

In another exemplary embodiment, the invention provides a method for screening compounds for modulation (e.g., agonists or antagonists) of the activity of hepcidin comprising administering to a transgenic animal (e.g., a transgenic animal having a transgene expressing hepcidin) a compound to be tested for its ability to modulate the amount of hepcidin; and determining the effect of the compound by measuring its effect on hepcidin levels in the animal. For example, using transgenic mice having a transgene expressing hepcidin, the expression inducing anaemia in the animal, compounds may be screened for the ability to modulate hepcidin activity and/or anaemia by reducing serum levels of hepcidin.

The hepcidin binding domain may be used in any in vitro binding assays, which are well known in the art, to quantify an amount of hepcidin or screen compounds for the ability to modulate hepcidin protein expression. Such modulators include, but are not limited to, small molecules, molecules from combinatorial libraries, antibodies or other proteins. The compounds may then be tested for modulation of hepcidin in vivo, in vitro, tissue culture or animal models. In an exemplary embodiment, the compounds are added to a plurality of cell cultures or animals and then tested using a method of the invention for their effect on hepcidin activity or serum levels. Compounds may also be screened for their ability to inhibit interaction of hepcidin with Fpn, for example, by their ability to disrupt or prevent binding of hepcidin to HBD. For example, a compound thought to inhibit binding of hepcidin to Fpn may be titrated into microtiter plate wells containing bound HBD and a known amount of labeled hepcidin then added, where inhibition of hepcidin binding to Fpn is exhibited by a decrease in the binding of labeled hepcidin relative to a control.

In yet another exemplary embodiment, the invention provides reagents for use in a diagnostic assay kit for the detection of a hepcidin protein, for example, in a biological sample obtained from a subject. In one exemplary embodiment, a hepcidin binding domain of the present invention may be used for the detection of hepcidin in a sample obtained from an individual, where detection and determination of hepcidin levels may be used to diagnose, prognose or predict haemochromatosis, iron deficiency anemia, hemosiderosis, liver cirrhosis and other iron homeostasis diseases or disorders.

The hepcidin binding domain peptide of the invention may be labeled, such as by conjugation, with enzymes (e.g., luciferase, as described in U.S. Pat. No. 4,614,712), antibodies, avidin, streptavidin, Fc binding proteins such as Protein A or G, biotin, affinity labels, fluorophores, fluorescent proteins (e.g., GFP and Keima) and/or radioactive isotopes to provide a detection signal. The hepcidin binding domain peptide may also be attached to a solid support, such as a bead or other such surface. For example, the hepcidin binding domain peptide may be attached to a bead comprising agarose, Ni-NTA-agarose, silica, protein A, Protein G, magnetic beads, chitosan, a gel, arginate, and other forms known in the art, or the hepcidin binding domain peptide may be attached, directly or indirectly, to other support surfaces, such as the plastic of a microtiter well. A label may be added to the hepcidin binding domain or the HBD attached to a solid support using methods known in the art, with or without bridging molecules, for example, as described in U.S. Pat. Nos. 5,055,561; 5,591,822; and 4,983,524.

Attachment of HBD to a solid support or immobilization of HBD may be conducted by any method involving cross-linkage formation which has been conventionally employed to prepare immobilized proteins (see U.S. Pat. No. 4,983,524).

Hepcidin bound to the HBD may also be chemically cross-linked to fix the protein interactions in place before quantifying hepcidin levels. Common cross-linking agents include, but are not limited to, a cleavable or non-cleavable NHS-ester (e.g., BS3), dithiobis (sulfosuccinimidyl propionate) (DTSSP), dimethyl dithiobispropionimidate (DTBP), and other cross-linking agents.

Assays that are suitable for use with the HBD of the invention include, but are not limited to, co-immunoprecipitation, western blotting, far-western analysis, fluorescence resonance energy transfer (FRET), bioluminescence resonance energy transfer (BRET), size exclusion liquid chromatography, pull-down assays, label transfer assays such as the Mts-Atf-Biotin or Sulfo-SBED biotin label transfer systems available from Thermo Scientific Pierce Protein Research Products, Dual Polarization Interferometry (DPI), Static Light Scattering (SLS) such as the automated system available from Wyatt Technology Corp., fluorescence, extinction coefficient, and protein assays such as absorbance at 280 nm or 205 nm, Lowry, Biuret, Bradford (coomassie based), Bicinchoninic Acid, Amido Black, or colloidal gold. For example, the HBD may be immobilized in a well of a 96-well microtiter plate, sample added to the well and incubated at 37° C. for a specified period of time, the sample removed, the well washed and bound hepcidin eluted, for example, by refrigeration, and the quantity of eluted hepcidin measured.

Table 1 provides general information regarding commonly used protein quantification methods.

TABLE 1

| Assay | Sensitivity | Accuracy | Interference |
| --- | --- | --- | --- |
| Biuret | 0-1 mg | Very high; independent of amino acid composition | Amino groups (e.g., $(NH_4)_2SO_4$) |
| Lowry | 0-0.1 mg | Partially dependent on amino acid composition | Acids, chelators (EDTA), reductants (DTT, phenol), $(NH_4)_2SO_4$ |
| Bradford | 0-0.01 mg | Dependent on amino acid composition | Detergents |
| BCA | 0-0.05 mg | Almost independent on amino acid composition | Reducing agents |

In an exemplary embodiment, a sample of blood is removed from a patient and placed in contact with an anticoagulant such as EDTA, mixed, centrifuged at about 600 g for about 10 min and the plasma removed, as is common in the art.

In an exemplary embodiment the HBD is used in any immunoassay system known in the art including, but not limited to: radioimmunoassays, enzyme-linked immunosorbent assay, "sandwich" assays, precipitation reactions, gel diffusion immunodiffusion assays, agglutination assays, fluorescent immunoassays, protein A immunoassays and immunoelectrophoresis assays (see U.S. Pat. No. 4,629,783 and patents cited therein).

For example, in a typical forward sandwich assay, unlabeled HBD is immobilized on a solid substrate, e.g., microtiter plate wells or agarose beads, and the sample to be tested is brought into contact with the bound HBD. After a suitable period of incubation (sufficient to allow formation of a hepcidin-HBD complex), an anti-hepcidin antibody labeled with a reporter molecule is then added and incubation is continued allowing the formation of a ternary complex of antibody-hepcidin-HBD. Unreacted material is washed away, and the presence of hepcidin is determined by observation of a signal from the reporter molecule. In another exemplary embodiment, the signal is quantitated by comparison with a control sample containing known amounts of hepcidin. Variations on the forward sandwich assay are well known to those skilled in the art and may be used with the HBD of the invention. This description of the typical forward sandwich assay merely indicates one possible method of using the HBD peptide in an immunoassay system and variations will be readily apparent in light of the present disclosure.

Since hepcidin is responsible for internalization of the iron exporter Fpn, inhibition of hepcidin may be effective in treating diseases characterized by elevated levels of hepcidin. Thus, the invention also relates to the use of HBD or peptidomimetics thereof for the treatment of an iron homeostasis disease or disorder and to the manufacture of medicaments comprising the HBD, which are useful for preventing and/or treating iron homeostasis diseases or disorders characterized by elevated levels of hepcidin, such as chronic renal insufficiency, anemia of inflammation and anemia of aging.

A variety of methodologies known in the art can be utilized to obtain or produce a hepcidin binding domain of the invention. See, e.g., Ausubel et al., Current Protocols in Molecular Biology. For example, a hepcidin binding domain can be produced by chemical synthesis using standard peptide synthesis methods known in the art and may include, amino acid alteration, substitution, replacement, insertion or deletion. Commercially available peptide synthesizers are particularly useful in producing small peptides and peptidomimetics that may be used according to the invention.

In other exemplary embodiments, production of a hepcidin binding domain can be achieved by recombinant DNA technology. For example, appropriate hepcidin nucleotide coding sequences may be synthesized, cloned and expressed in appropriate host cells. Methods that are well known to those skilled in the art can be used to construct expression vectors containing a hepcidin binding domain and appropriate transcriptional/translational control signals. These methods include in vitro recombinant DNA techniques, synthetic techniques and in vivo recombination/genetic recombination.

A variety of host-expression vector systems may be utilized to express a hepcidin binding domain. These include but are not limited to microorganisms such as bacteria transformed with recombinant bacteriophage DNA, plasmid DNA or cosmid DNA expression vectors containing a coding sequence for a hepcidin binding domain; yeast, insect cell systems, or animal cell systems transformed or infected with recombinant expression vectors, including viral expression vectors (e.g., baculovirus, adenovirus, and vaccinia virus), containing a coding sequence for a hepcidin binding domain. The transcriptional/translational control signals of these vectors vary in their strength and specificities, as is understood in the art. Depending on the host/vector system utilized, any of a number of suitable transcription and translation elements, including constitutive and inducible promoters, may be used in the expression vector (see U.S. Patent Publication 20040096990 and references cited therein).

Peptidomimetics of the invention include, but are not limited to, the following modifications of HBD: modifications to the N and C terminal ends of the peptide; changes of the side chain, which can involve amino acid substitutions; modification in the α carbon including methylations, alkylations and dehydrogenations; chirality changes by replacing D residue with an L residue; head to tail cyclizations; introduction of amide bond replacements, i.e., changing the atoms participating in the peptide (or amide) bond, and combinations thereof (see U.S. Pat. Nos. 6,462,171 and 5,948,763).

The presence of non-natural amino acids usually increases peptide stability. In addition, at least one of these amino acids, a aminoisobutyric acid or Aib, imposes significant constraints to model peptides diminishing their conformational flexibility.

The most commonly used a carbon modification to improve peptide stability is α methylation. In addition, replacement of the hydrogen atom linked to the α carbon of Phe, Val or Leu has been shown to favor the adoption of β bend conformation and strongly disfavor the formation of β pleated sheet structures. According to the present invention, methylation of those residues in the inhibitor peptides is expected to enhance stability and potency.

Replacement of the natural L residue by a D enantiomer dramatically increases resistance to proteolytic degradation.

Conformationally constrained cyclic peptides may represent better drug candidates than linear peptides due to their reduced conformational flexibility and improved resistance to exopeptidase cleavage. Two alternative strategies have been used to convert a linear sequence into a cyclic structure. One is the introduction of cysteine residue to achieve cyclization through the formation of a disulfide bridge and the other is the side chain attachment strategy involving resin bound head to tail cyclization.

Amide bond surrogates refers to peptides containing chemical modifications of some (or all) of the peptide bonds. Amide bond replacements are usually represented by retaining the amino acid designation according to the side chain and specifying the changes that occur between the α carbons. Several amide bond surrogates are described in Table 2 below.

TABLE 2

Some amide bond surrogates and their properties

| Surrogate | Properties |
|---|---|
| $CH_2$ | Short, flexible |
| $CH_2CH_2$ | Flexible, hydrophobic |
| CH═CH | Rigid, hydrophobic |
| C≡C | Very rigid |
| $CH_2NH$ | Flexible, hydrophilic |
| $COCH_2$ | Flexible, hydrophilic |
| $CH_2S$ | Flexible, hydrophobic |
| $CH_2SO_2$ | More rigid, hydrophilic |
| NHCO | Rigid, hydrophilic |

Another approach to improve stability, which also may result in the generation of orally active compounds, is to produce a molecule that mimics the biological activity of the peptide, but is no longer a peptide in chemical nature (i.e., no longer contains peptide bonds). The term peptidomimetic is used herein to describe molecules that are partially peptide in nature, such as pseudopeptides, semi peptides or peptoids, as well as an organic molecule that no longer contains any peptide bonds.

The compound of the invention may be administered by any means that achieves its intended purpose. For example, administration may be by a number of different parenteral routes including, but not limited to, subcutaneous, intravenous, intradermal, intramuscular, intraperitoneal, intracerebral, intranasal, oral, transdermal, or buccal routes. Parenteral administration can be bolus injection or by gradual perfusion over time.

The dosage administered will be dependent upon the age, sex, health, and weight of the recipient, kind of concurrent treatment, if any, frequency of treatment, and the nature of the effect desired. The total dose required for each treatment may be administered by multiple doses or in a single dose. By "effective amount," it is meant a concentration of the compound which is capable of slowing down or inhibiting the interaction of hepcidin with Fpn in a subject. Such concentrations can be routinely determined by those of skill in the art. It will also be appreciated by those of skill in the art that the dosage may be dependent on the stability of the administered compound. A less stable compound may require administration in multiple doses or larger doses.

Preparations for parenteral administration include sterile aqueous or non-aqueous solutions, suspensions and emulsions, which may contain auxiliary agents or excipients which are known in the art. Pharmaceutical compositions such as tablets and capsules can also be prepared according to routine methods.

Pharmaceutical compositions comprising the compound of the invention include all compositions wherein the compound is contained in an amount effective to achieve its intended purpose. In addition, the pharmaceutical compositions may contain suitable pharmaceutically acceptable carriers comprising excipients, diluents and auxiliaries which facilitate processing of the active compounds into preparations which can be used pharmaceutically. Suitable pharmaceutically-acceptable vehicles are well known in the art and are described for example in Gennaro, Alfonso, Ed., Remington's Pharmaceutical Sciences, 18th Edition 1990, Mack Publishing Co., Easton, Pa. Pharmaceutically-acceptable vehicles can be routinely selected in accordance with the mode of administration and the solubility and stability of the compound. For example, formulations for intravenous administration may include sterile aqueous solutions which may also contain buffers, diluents and other suitable additives.

The invention is further illustrated by the following description and examples, which are for illustrative purposes only.

Binding of hepcidin to Fpn leads to the internalization and degradation of Fpn and removal of Fpn from cell surfaces preventing cellular iron export (2). Hepcidin binding leads to the phosphorylation of two adjacent tyrosines present in an intracellular loop formed between the 6 and 7 putative transmembrane domains of Fpn. Based on the behavior of a human Fpn mutant (C326Y) that does not bind hepcidin, it was hypothesized that the HBD might be on the predicted adjacent extracellular domain (aa 324-343) (3). A peptide containing the predicted HBD was synthesized and shown to bind $^{125}$I-hepcidin, while an HBD peptide containing the human Fpn mutation C326Y did not bind $^{125}$I-hepcidin.

Hepcidin binds to Fpn (2) or the I-HBD in a temperature dependent manner. Initially it was thought that the lack of binding of hepcidin to Fpn-GFP expressing cells at low temperature reflected weak binding, and that the association of hepcidin with cells at 37° C. reflected the capture of hepcidin through internalization of the hepcidin-Fpn complex. The data herein shows that the binding of hepcidin and Fpn at low temperature reflects a greatly increased rate of dissociation of the Fpn-hepcidin complex, where at 37° C. the binding of hepcidin to Fpn shows an immeasurably slow rate of dissociation. Furthermore, the increased rate of dissociation of hepcidin from Fpn or HBD is due to the temperature sensitivity of hepcidin structure and not the HBD. Hepcidin at physiological temperatures shows a definitive structure as assessed by CD and NMR (7, 8, and 10). The structure of hepcidin shows a distorted β-sheet shape with a hairpin loop. The β-sheet structure is stabilized by disulfide pairing of cysteine residues and hydrogen bonding between the two antiparallel strands leading to a markedly amphipathic peptide structure. At low temperature CD and NMR analysis shows that hepcidin becomes less structured. The structural change in hepcidin may permit the formation of hepcidin dimers, which are unable to bind to Fpn.

The five amino terminal amino acids of hepcidin were previously shown to be critical for binding of hepcidin to Fpn (7). Similarly, Hep20, which lacks the five amino terminal amino acids, does not bind to I-HBD. In addition, CD analysis shows that the amino terminal five amino acids play a critical role in hepcidin structure, as removal of those five amino acids prevents the low temperature structural changes in hepcidin. Hepcidin is amphipathic and it is hypothesized that the hydrophobic surface of hepcidin monomers are interacting at 4° C. to form a dimer. Hepcidin, like other defensins, interacts through its hydrophobic surface with bacterial membranes (11). In a preliminary study the inventors determined that the low temperature hepcidin dimer cannot bind to *E. coli*, suggesting again that the hydrophobic face of hepcidin is occluded.

The data herein also shows that the I-HBD can be used to assay hepcidin in biologic fluids. Further, since I-HBD does not bind Hep20, but does bind Hep25, the assay focuses on the bioactive form of hepcidin. Data is presented showing that this assay can detect variations in serum hepcidin levels due mutations in genes known to affect hepcidin levels, including HAMP and Hemojuvelin, mutations in other genes involved in iron metabolism (HFE) and LPS stimulation. It is interesting to note that mice heterozygous for a deletion in HAMP only show a 30% reduction in serum hepcidin suggesting that some allelic compensation might be occurring. This result is consistent with the normal iron levels found in Hep+/− mice. Hfe−/− mice show low levels of serum hepcidin suggesting that the loss of HFE results in significant changes in HAMP expression, hepcidin synthesis or hepcidin secretion. The sensitivity and rapidity of the I-HBD hepcidin assay offers a facile approach to determining hepcidin levels, particularly in serum and other biological fluids.

Example I

Based on the behavior of Fpn mutants, the putative hepcidin binding domain (HBD) on Fpn was identified. A peptide with the sequence of the binding site was synthesized and used to shown that the interaction of hepcidin with this peptide faithfully recapitulates the characteristics of hepcidin binding to Fpn expressing cells. The present studies show that binding of hepcidin to the hepcidin binding site on Fpn (HBD) is driven by hydrophobic interactions as shown by its extraordinary sensitivity to low temperature. The temperature sensitivity of the hepcidin-Fpn interaction is driven by the temperature sensitivity of hepcidin structure. Additionally, it is shown that the binding of hepcidin to an immobilized HBD peptide can be used to assay hepcidin in biological fluids.

Most of the reported Fpn mutations that lead to hepatic iron overload disease are able to bind hepcidin (6). There are three Fpn mutations, however, that show no measurable binding of hepcidin. The mutations are missense mutations at position C326 (C326Y/T/S). This mutation site is in the extracellular loop, which is just distal to the predicted cytosolic loop containing the two adjacent tyrosines that are phosphorylated in response to hepcidin binding (3). It was hypothesized that this Fpn extracellular loop may contain the HBD.

To test this hypothesis a 20 amino acid peptide corresponding to the sequence of the extracellular loop was synthesized (SEQ ID NO: 2) and assayed to determine whether this peptide would compete with cell surface Fpn for hepcidin binding. In addition, control peptides were also synthesized. The peptide sequences are shown in Table 3.

Figure 1B:
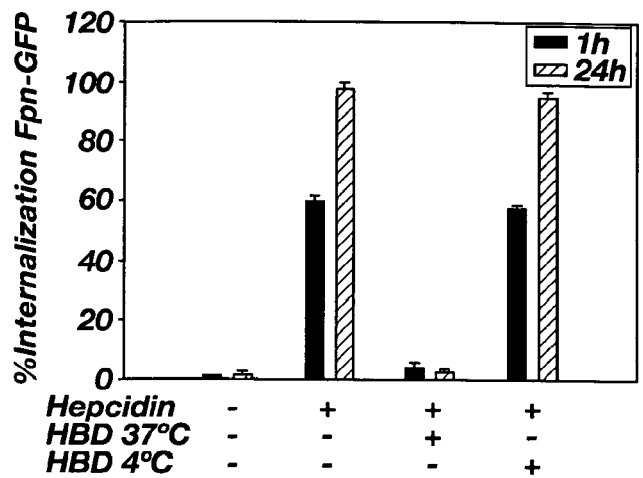

Incubation of HEK293TFpn-GFP cells with hepcidin results in the internalization of cell surface Fpn-GFP (2) and FIG. 1A. Preincubation of equal molar amounts of HBD (SEQ ID NO: 2) with hepcidin prevented hepcidin-mediated internalization of Fpn-GFP. Decreased hepcidin-mediated internalization of Fpn-GFP in response to HBD preincubation was not the result of a generalized inhibition of endocytosis, as cells incubated with HBD were capable of pinocytosing fluorescent dextran similar to cells without HBD (data not shown). Preincubation of hepcidin with a peptide containing the same amino acid composition as HBD but in a randomized sequence ("Scramble") (SEQ ID NO: 3) did not prevent Fpn-internalization. Preincubation with a Fpn peptide containing the C326Y mutation (HBD mutant) (SEQ ID NO: 4) did not prevent hepcidin mediated Fpn-GFP internalization. Previously it was determined that hepcidin binding to Fpn was temperature dependent (2). Preincubation of HBD with hepcidin at 4° C. did not prevent the time-dependent internalization of Fpn-GFP (FIG. 1B).

TABLE 3

| Peptide | Sequence | Molecular Weight (Da) |
|---|---|---|
| HBD wt | RR-FDCITTGYAYTQGLSGSILS-RR (SEQ ID NO: 2) | 2722 |
| HBD Scramble | RR-ILSLFDAYCTGTQITGSGSY-RR (SEQ ID NO: 3) | 2722 |
| HBD Mutant | RR-FDYITTGYAYTQGLSGSILS-RR (SEQ ID NO: 4) | 2782 |

Materials and Methods:

HEK293TFpn-GFP, a stable cell line in which Fpn-Green fluorescent protein (GFP) expression is regulated by the ecdysone promoter has been described previously (2).

Peptides were synthesized at the DNA/Peptide Core Facility, University of Utah, Salt Lake City, Utah. The peptide sequences and their masses are reported in Table 3. The peptides were synthesized with two arginines added at the amino and carboxyl terminals. The addition of the arginines increased the solubility of the peptide but did not affect the specificity, temperature dependence or affinity of the HBD for hepcidin. Microscope analysis was carried out using an Olympus BX51 microscope (Olympus, Tokyo, Japan). Images were acquired using Picture Frame 2.5 software (Olympus America, East Muskogee, Okla.). All experiments were repeated a minimum of 5 times.

Example II

Figure 1C:
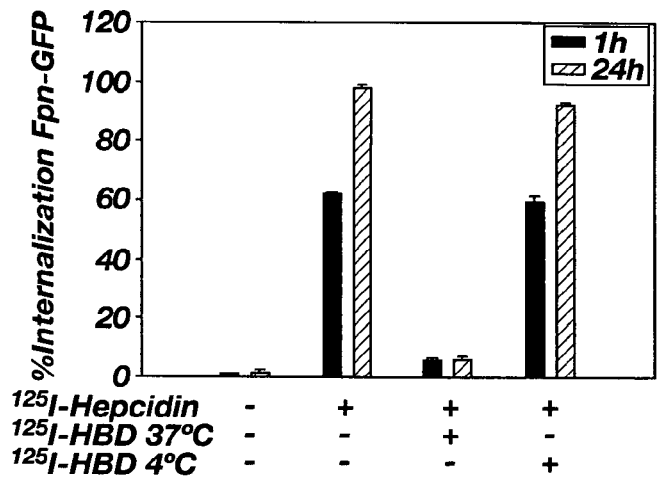
Figure 1D:
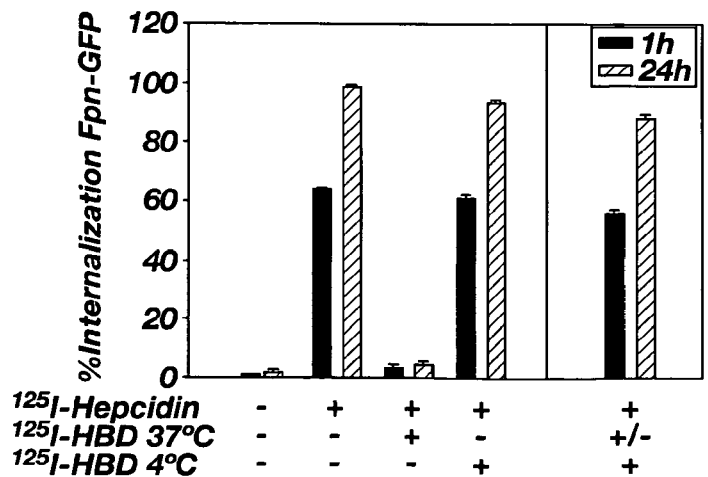

To characterize the interaction of the HBD with hepcidin, hepcidin was labeled at an iodinateable tyrosine to produce $^{125}$I-hepcidin. Previously, it was shown that $^{125}$I-hepcidin bound to Fpn indistinguishably from hepcidin that lacked the iodinateable tyrosine (2). HBD was then conjugated to agarose beads to produce immobilized HBD (I-HBD), which was then preincubated with $^{125}$I-hepcidin at 37° C. prior to addition to Fpn-GFP expressing cells. Preincubation of $^{125}$I-hepcidin with I-HBD followed by the removal of the I-HBD beads led to loss of Fpn-GFP internalization activity (FIG. 1C) suggesting that $^{125}$I-hepcidin was bound to I-HBD and not available to bind the Fpn-GFP on the cell surface. Preincubation of $^{125}$I-hepcidin with either scrambled HBD (SEQ ID NO: 3) or HBD containing the Fpn C326Y mutation (SEQ ID NO: 4) did not affect the ability of $^{125}$I-hepcidin to induce internalization of Fpn-GFP. There was no loss of internalization activity when I-HBD was incubated with $^{125}$I-hepcidin at 4° C. Most strikingly, preincubation of I-HBD with $^{125}$I-hepcidin at 37° C. followed by a shift of the I-HBD/$^{125}$I-hepcidin complex to 4° C. resulted in the recovery of hepcidin-mediated Fpn-GFP internalization activity (FIG. 1D). These results suggest that hepcidin can bind to I-HBD at 37° C., but the binding is unstable at low temperature.

Figure 2A:
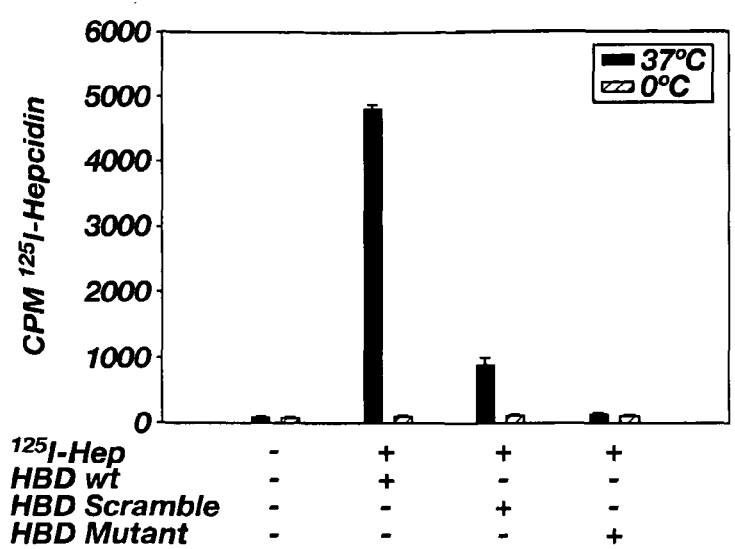
FIGS. 2A-C illustrates that the binding of $^{125}$I-hepcidin to HBD is specific and temperature dependent.
Figure 2B:
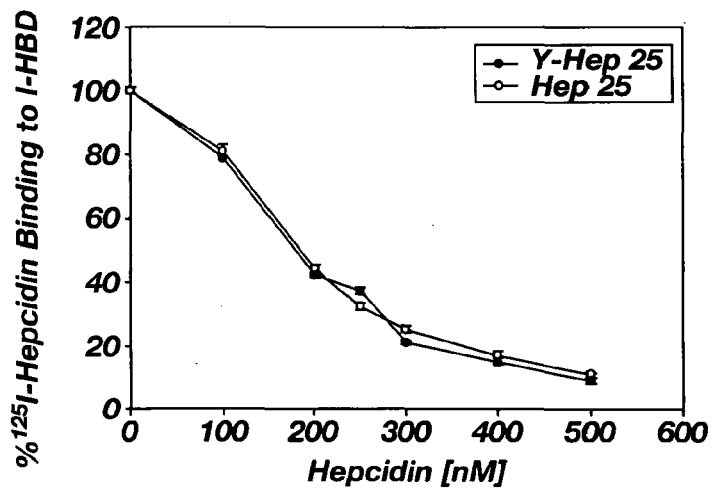
Figure 2C:
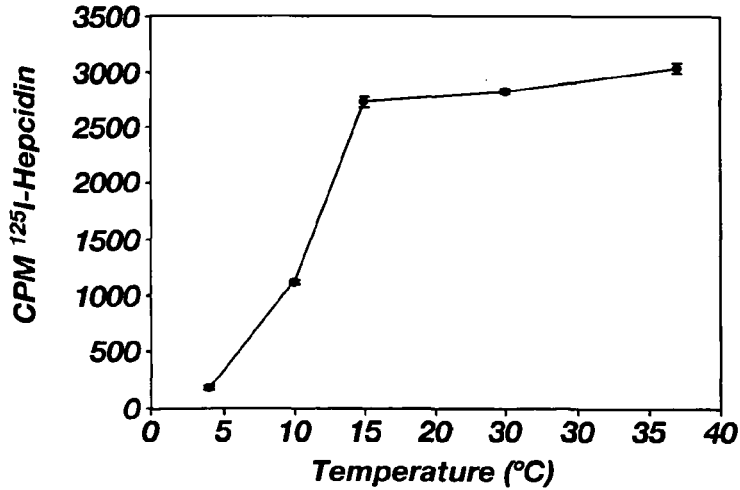

$^{125}$I-hepcidin binding to I-HBD, but not to beads containing scrambled HBD or C326Y-HBD (FIG. 2A), was also confirmed. The binding of $^{125}$I-hepcidin could be reduced by addition of native non-radioactive hepcidin with an apparent K of approximately 200 nM (FIG. 2B). There was no binding of $^{125}$I-hepcidin to I-HBD at 4° C. and $^{125}$I-hepcidin bound to I-HBD at 37° C. was released when subsequently placed at 4° C. (data not shown). Examination of the binding of $^{125}$I-hepcidin to I-HBD as a function of temperature shows that at temperatures below about 15° C. binding was decreased dramatically (FIG. 2C).

Figure 3A:
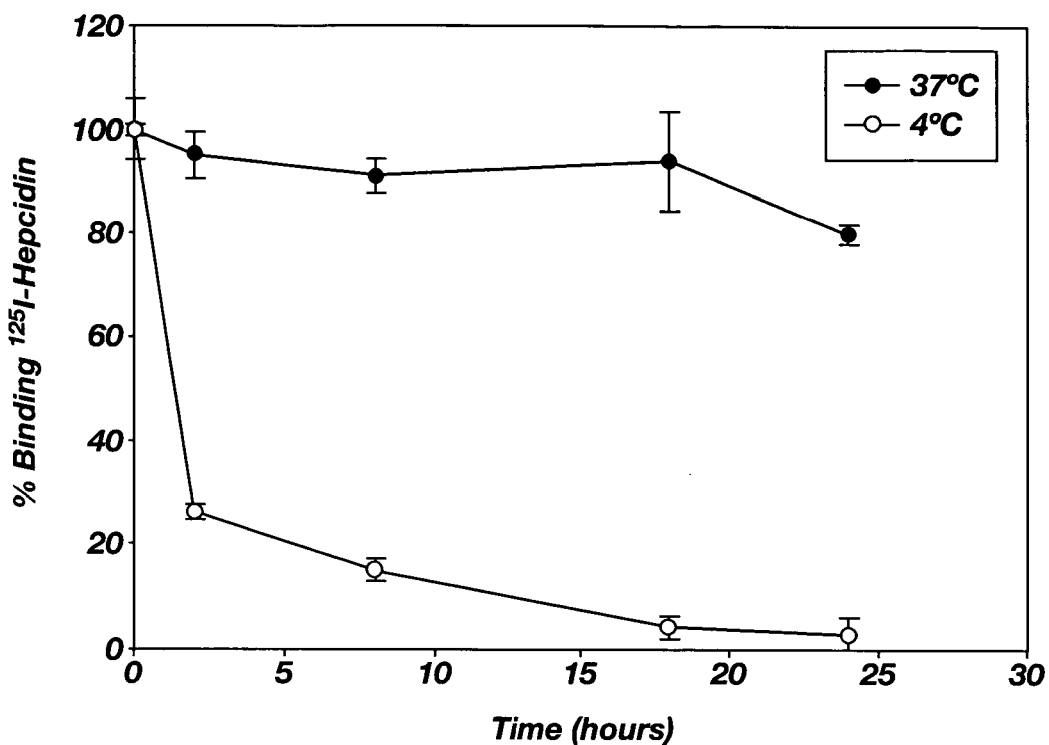
FIGS. 3A and 3B illustrate that the dissociation of the hepcidin/HBD complex is accelerated by low temperature.
Figure 3B:
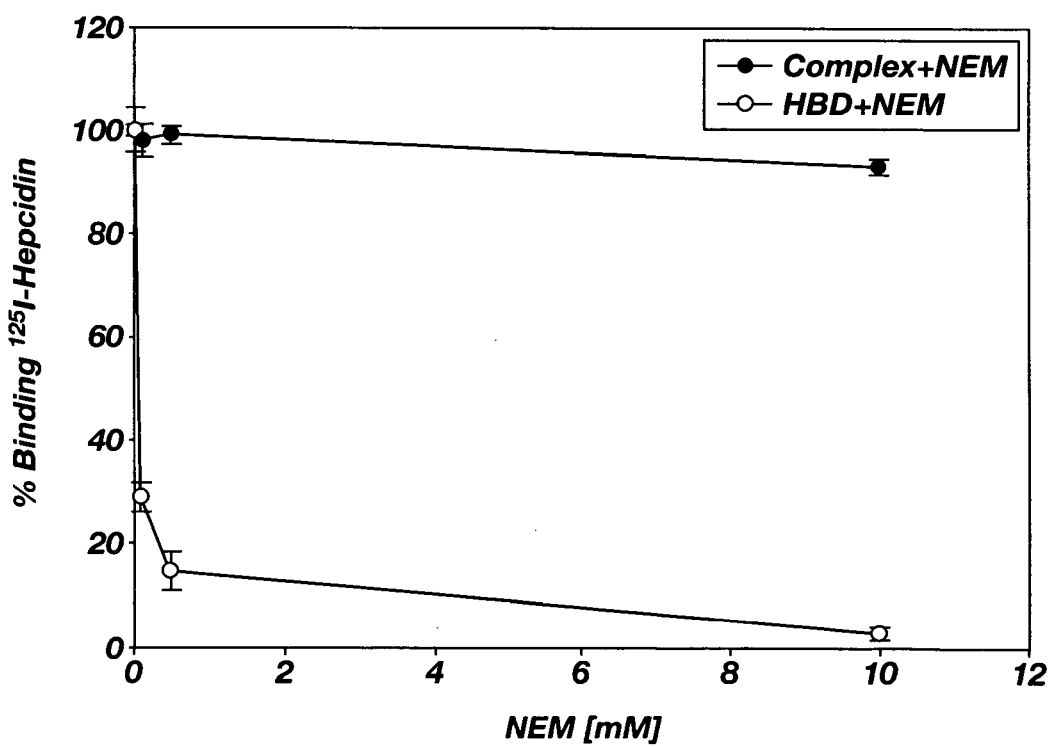

The $^{125}$I-hepcidin-I-HBD complex was extraordinarily stable at 37° C., even in the presence of a large molar excess of non-radioactive hepcidin, there was little dissociation of the $^{125}$I-hepcidin/I-HBD complex over a time course of 18 hours (FIG. 3A). However, if the $^{125}$I-hepcidin-I-HBD complex formed at 37° C. was shifted to 4° C. there was a rapid dissociation of the $^{125}$I-hepcidin-I-HBD complex. Furthermore, treatment of I-HBD with the alkylating agent N-ethylmaleimide (NEM) led to a loss of $^{125}$I-hepcidin binding activity (FIG. 3B), again suggesting that the free cysteine in I-HBD is required for hepcidin binding. If a $^{125}$I-hepcidin/I-HBD complex was formed at 37° C. and then NEM added, the complex was not affected by the alkylating agent. These results indicate that binding of hepcidin to I-HBD prevents NEM from having access to the free cysteine in HBD. These results are also consistent with the absence of disulfide bond formation or interchange between the cysteines in hepcidin and the cysteine in the HBD.

Materials and Methods:

HBD peptides were immobilized by covalently attaching them to agarose beads. Immobilization was performed using AminoLink Plus Immobilization Kit (Pierce) following the manufacturer's instructions. 1.0 mg of HBD peptide was used per 2.0 ml of AminoLink beads. To measure hepcidin concentrations in biological fluids, samples were mixed with a defined concentration of $^{125}$I-hepcidin and then added to HBD conjugated beads. The samples were incubated at 37° C. or 4° C. for 18 hours. The beads were washed multiple times with phosphate buffered saline to remove unbound $^{125}$I-hepcidin by centrifugation for two min at 1500 rpm. The fluid was removed and the radioactivity bound to beads was determined by gamma counting (Perkin/Elmer).

Hepcidin was synthesized and iodinated as described (2).

Protein concentrations were measured using the BCA assay (Pierce, Rockford, Ill.). Protein measurements were performed on the HBD prior to binding and on the supernatant of a centrifuged I-HBD. The difference in protein levels between the two measurements is the amount conjugated to the bead.

Example III

Figure 4A:
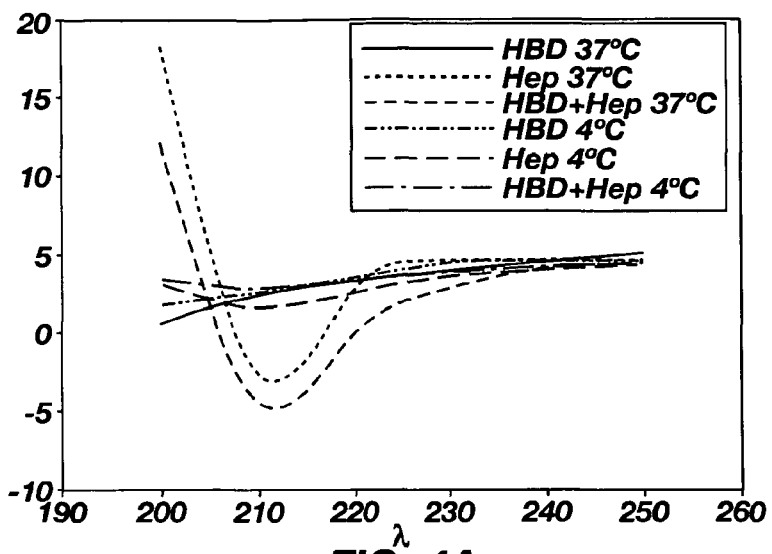
FIGS. 4A-C illustrate the temperature-dependent changes in hepcidin structure.
Figure 4B:
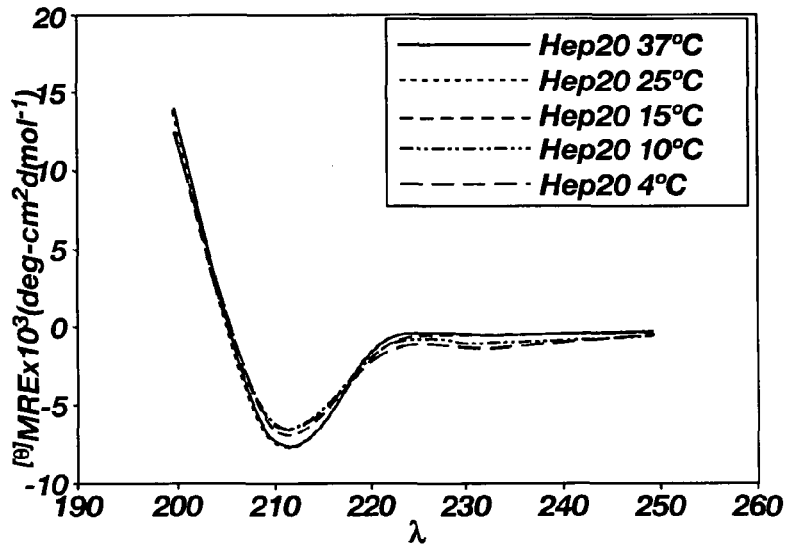
Figure 4C:
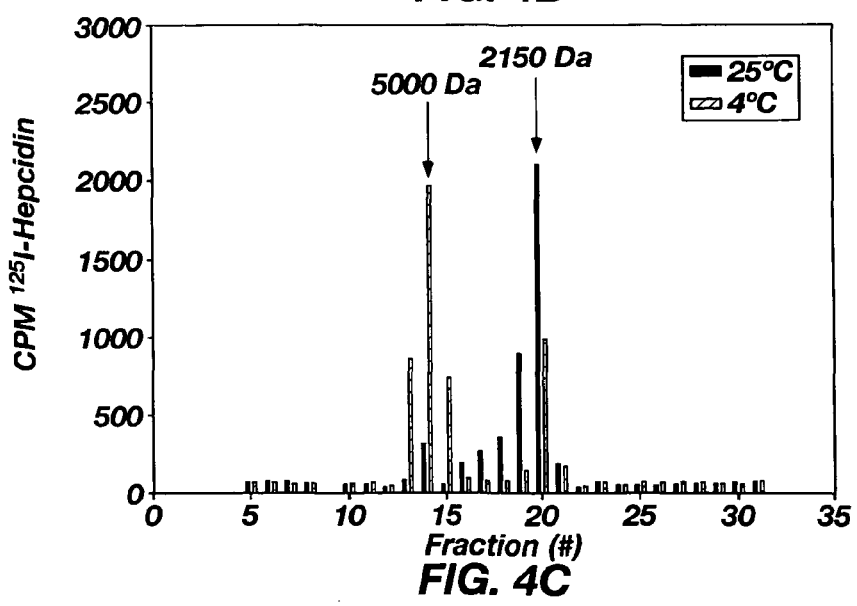

To understand the temperature sensitivity of hepcidin binding, the properties of hepcidin and HBD were examined by CD spectroscopy. Hepcidin showed mostly β-sheets with a small amount of α-helical structure when measured at 20° C. or higher (FIG. 4A), a result consistent with published studies (7). An equal molar mixture of HBD and hepcidin had a CD spectrum similar to that of hepcidin alone. When measured at 4° C., however, there was little CD structure for the hepcidin-HBD mixture or for hepcidin alone. These results indicate that the structure of hepcidin is temperature sensitive. The major change in hepcidin structure occurs at about 10° C. (FIG. 4A small insert). The change in hepcidin structure also occurs at about the same temperature where hepcidin binding to HBD shows a dramatic change (see FIG. 2D). These results suggest that the dissociation of hepcidin from the hepcidin/HBD complex is the result of a change in hepcidin structure. The temperature dependent change in hepcidin structure also results in a change in the multimerization state of hepcidin. Previous studies indicated that hepcidin formed multimers in a concentration dependent manner (8). At the concentrations employed in this study and at about 20° C. hepcidin is a monomer, as shown by size exclusion chromatography (FIG. 4C). When the same preparation of hepcidin was incubated at 4° C. and then applied to size exclusion chromatography hepcidin formed a dimer Materials and Methods:

Circular dichroism spectra (200-250 nm) of 100 μM hepcidin, Hep20 (five amino terminal amino acids deleted) and HBD in 50 mM sodium phosphate buffer pH 7.2 were recorded on an AVIV 62DS spectrometer (AVIV, Lakewood, N.J.). Samples were scanned at temperatures of 37-25-15-10-4° C. using a 1 mm path length cell (Starna Cells, Calif.). Before analysis, spectra were baseline corrected by subtracting spectra of sample-free buffer solution from the peptide-containing sample.

For gel-filtration chromatography $^{125}$I-hepcidin was applied to a column G-25 Superfine (Amersham Pharmacia) equilibrated in phosphate buffered saline (PBS). The column was calibrated using insulin (5808 Da, Sigma), diazepam binding inhibitor (DBI) Fragment 51-70 human (2150 Da, Sigma) and neurotensin (1672 Da, Sigma) as standards. Fractions (200 μL) were collected and analyzed for $^{125}$I-hepcidin by gamma counting (Perkin/Elmer) and SDS-PAGE analysis, followed by Coomassie Blue staining (Pierce) for the molecular weight standards.

Example IV

Derivatives of hepcidin, which lack the first five amino acids (Hep20) do not bind to Fpn (7) nor do they bind to HBD (data not shown). CD analysis of Hep20 shows a spectrum that was identical to that of hepcidin when assayed at 20° C. (7). In contrast to hepcidin, the Cd spectrum of Hep20 did not change when assayed at 4° C. (FIG. 4B), nor did Hep20 show temperature dependent multimerization when assayed by molecular size chromatography (data not shown). These results suggest that the temperature-dependent changes in hepcidin structure require the presence of the amino terminal domain of hepcidin.

Example V

Figure 5A:
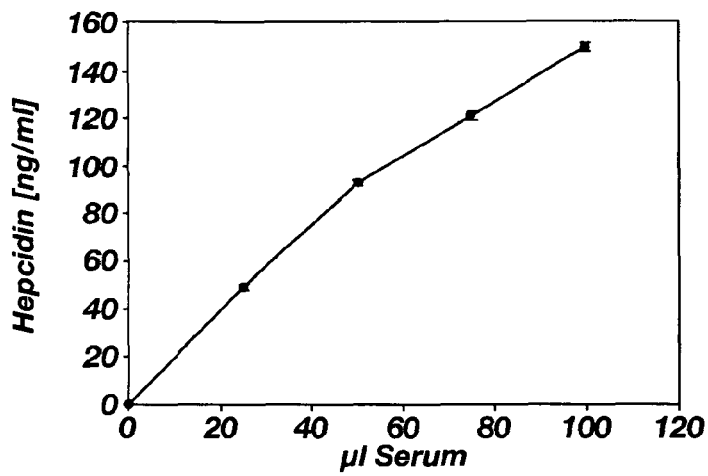
FIGS. 5A-E illustrate the hepcidin concentrations in mice and human sera.
Figure 5B:
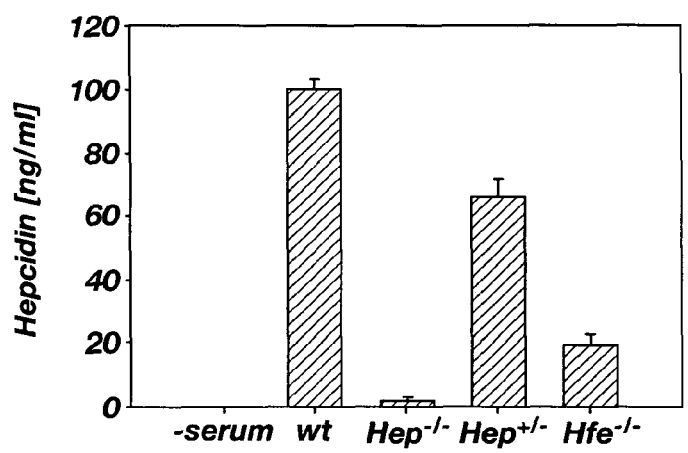
Figure 5C:
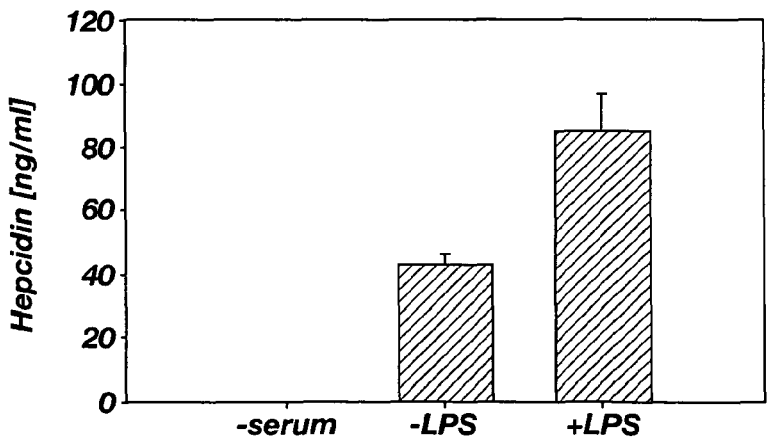
Figure 5D:
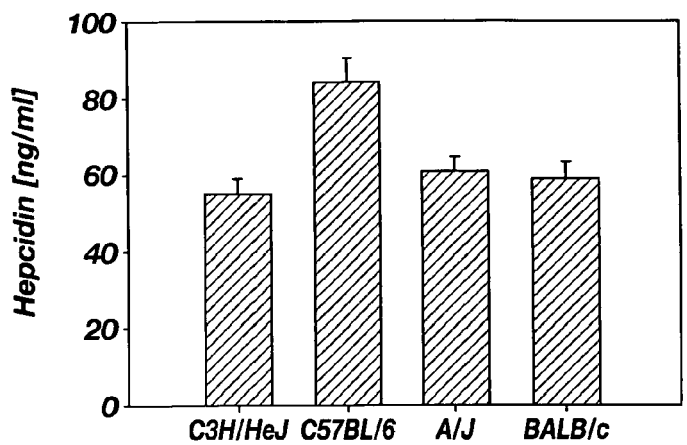
Figure 5E:
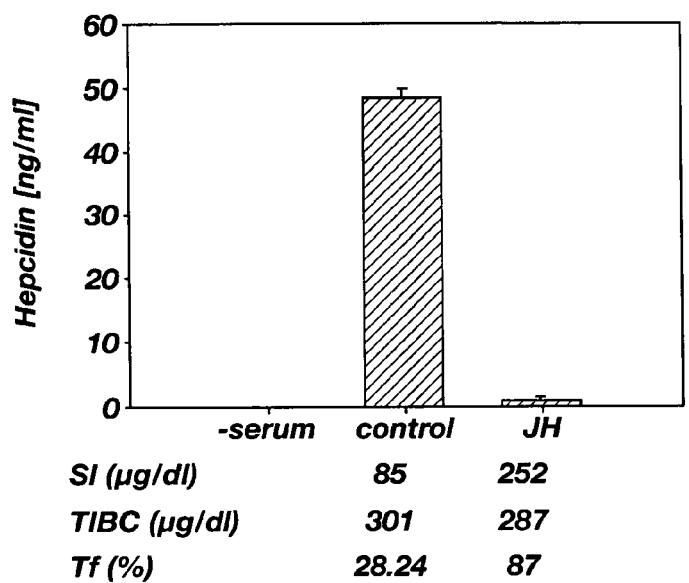

The results herein show that binding of $^{125}$I-hepcidin to I-HBD may be used to assay hepcidin concentrations in vitro assay fluids. To further confirm this aspect of the invention and confirm its application to biological fluids, the level of hepcidin was measured in murine serum obtained from wild type mice, mice homozygous (Hep−/−) and heterozygous (Hep+/−) for a targeted HAMP (Hep gene) deletion or mice homozygous for a targeted deletion in the HFE gene (Hfe−/−) (FIG. 5B). The ability of wild type serum to compete with $^{125}$I hepcidin for binding was also assayed (FIG. 5A). Extrapolation of the data showed that sera obtained from wild type C57/Bl6 mice contained approximately 100 ng/ml hepcidin (FIG. 5B). Serum from Hep−/− mice had essentially undetectable levels of hepcidin, while Hep+/− mice showed 70% of normal values. Hfe−/− mice showed lower levels of hepcidin than the Hep+/− mice. To further demonstrate that the hepcidin assay could measure changes in serum hepcidin levels, LPS was injected into C57/Bl6 mice, serum was harvested 8 hours post injection, and hepcidin levels were measured (FIG. 5C). Sera from LPS injected mice showed a two-fold increase in hepcidin levels (FIG. 5C). We have also used the assay to show that genetically different strains of mice have different steady state levels of hepcidin (FIG. 5D). To demonstrate the application of the assay in human subjects, hepcidin levels in human serum were also measured. Serum from a population of normal females showed an average of 50 ng/ml hepcidin, while an age matched individual with juvenile hemochromatosis (JH) with known mutations in HJV (9) showed 2 ng/ml hepcidin. These data confirm that HBD (e.g., I-HBD) can be used to assay hepcidin levels in biological fluids.

Materials and Methods:

Measurements of serum ferritin and transferrin saturation were performed as described (5). All animal studies were approved by the Animal Research Committee at University of Utah. C3H mice were injected with lipopolysaccharide (LPS, Sigma) and sacrificed 10 hours later. Animals were euthanized and blood was collected by cardiac puncture. The mice (C57/Bl6 and C3H) and human sera samples were collected in accordance with the Institutional Animal Care and Use Committee and the Institutional Review Board.

Example VI

Figure 6:
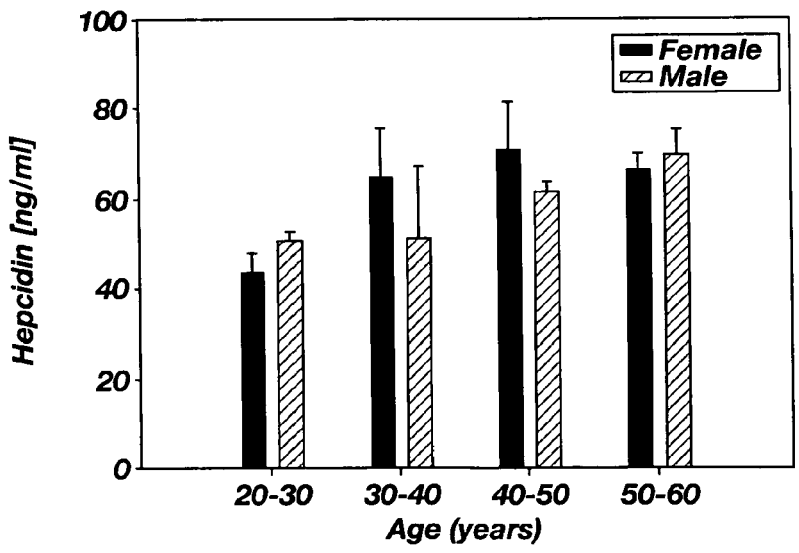

FIG. 6 illustrates hepcidin levels in previously frozen patient serum versus patient age and gender, as determined using the I-HBD binding assay. Note that hepcidin levels increase with age; this may be important for the anemia of aging.

Example VII

In accordance with the invention, HBD can be used in an assay system to determine levels of hepcidin in a test sample. Accordingly, unlabeled HBD is immobilized on a solid substrate. HBD peptides were immobilized by covalently attaching them to a 96-well plate. Immobilization was performed using Reacti-Bind Amine-binding 96-well plates (Pierce), following the manufacturer's instructions. In this example, 20 μg/ml re-suspended HBD peptide was immobilized in 96 well plates in an immobilization phosphate buffered saline (pH 7.5). 100 μl of peptide solution was added to each well. The plates were incubated at room temperature overnight. The peptide solution was then removed from the wells and a protein blocking buffer, such as dry milk in phosphate buffer saline, was added to each well and allowed to sit for two hours at 37° C. The plates were then washed with warm washing buffer to remove unbound material.

Figure 7:
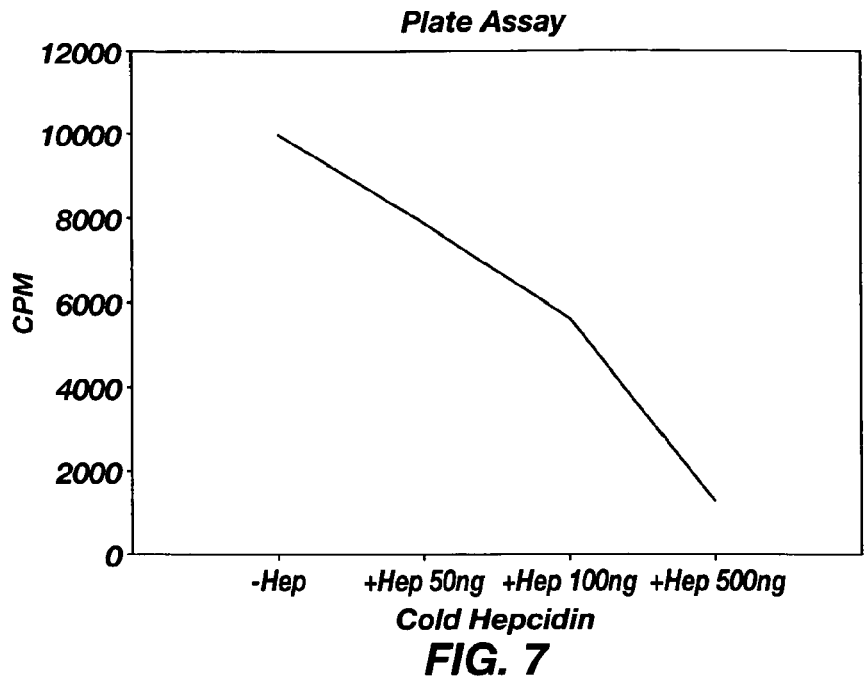
In FIG. 7, hepcidin binding to I-HBD bound in the wells of a 96-well plate is determined, and unlabelled hepcidin is shown to compete with the labelled hepcidin for binding to the plate.

HBD-coated plates were used in an assay to detect hepcidin as follows: Samples containing 0, 50, 100, and 500 ng of hepcidin were spiked with 1125-labeled hepcidin (10,000 cpm) and added to the wells of the HBD-coated plate. The plate was incubated at room temperature for 4 hours. Following the incubation, unbound material was removed from the wells, and the amount of $^{125}$-labeled hepcidin remaining bound to the plate was determined by gamma counter. As sample hepcidin levels increase, the amount of bound $I^{125}$-labeled hepcidin decreases, indicating that unlabeled hepcidin is able to compete for binding to I-HBD. (FIG. 7)

Hepcidin labeled with other reporter conjugates, such as biotin, or chemiluminescent or fluorescent labels, could be substituted for the $I^{125}$ hepcidin to allow detection using streptavidin conjugates, or direct detection of chemiluminescent or fluorescent signal. Alternatively, following incubation of samples in the wells of the plate, anti-hepcidin antibody could be used to detect hepcidin bound to the plate. For example, anti-hepcidin antibody labeled with a reporter molecule might be added and incubated so that a ternary complex of antibody-hepcidin-HBD was allowed to form. Following washing to remove unbound material, the presence of hepcidin would be determined by detection of a signal from the reporter molecule per known methods.

Example VIII

Figure 8A:
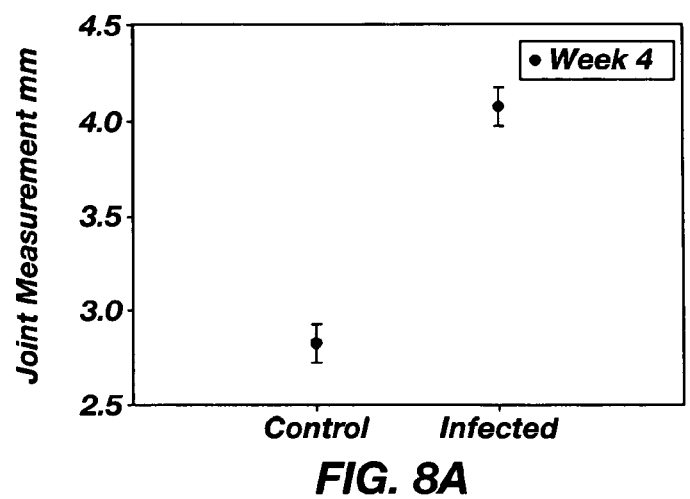
FIGS. 8A-8E illustrate data collected from mice and humans that were infected with Lyme disease and presented with symptoms of the disease, including arthritis.
Figure 8B:
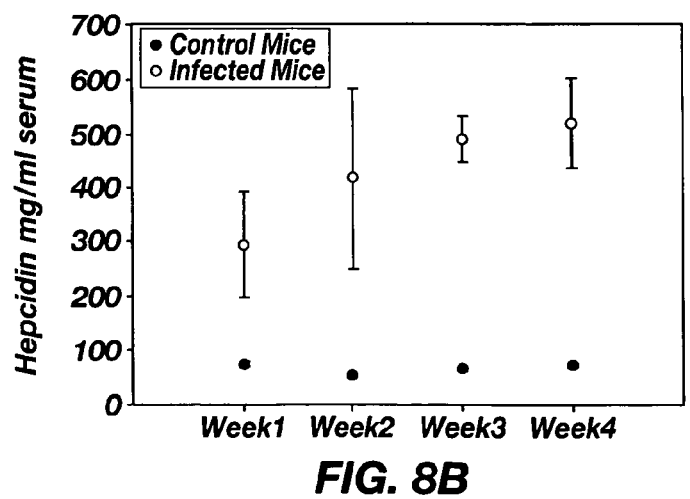
Figure 8C:
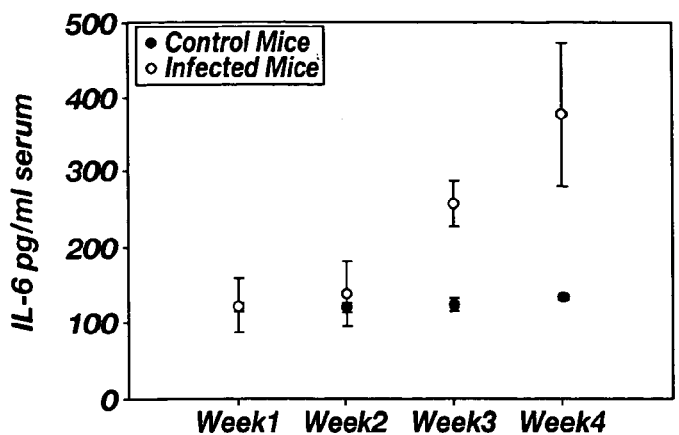

Lyme disease, or borreliosis, is an emerging infectious disease in humans and other animals. *Borrelia burgdorferi* is the predominant cause of Lyme disease. Lyme arthritis has been postulated to be related to or mediated by hepcidin activity. Thus, levels of hepcidin in mice having Lyme disease-inducing arthritis were determined. Mice were injected with *Borrelia* and sera samples were analyzed every week for four weeks. At week 4, the control mice and infected mice were sacrificed, and joint measurement was calculated to determine the severity of the infections. The results of the joint measurement evaluations are shown in FIG. 8A. Hepcidin levels in the mice were measured using the HBD-beads in coded samples, as established in the assay described in Example II, hereinabove. The levels of hepcidin in sera of infected mice were shown to be significantly higher than the control mice, as shown in FIG. 8B. For comparison purposes, serum levels of the cytokine Interkukin-6 (IL-6) were analyzed, by known methods, e.g. an ELISA assay, as an inflammatory marker using sera samples extracted from the same mouse groups as used for the previously described hepcidin analysis. The results of the IL-6 serum level analysis are shown in FIG. 8C, which indicate that use of hepcidin serum levels provides a better indicator of disease condition as a diagnostic or prognosis indicator than conventionally known analyses.

Example XI

Figure 8D:
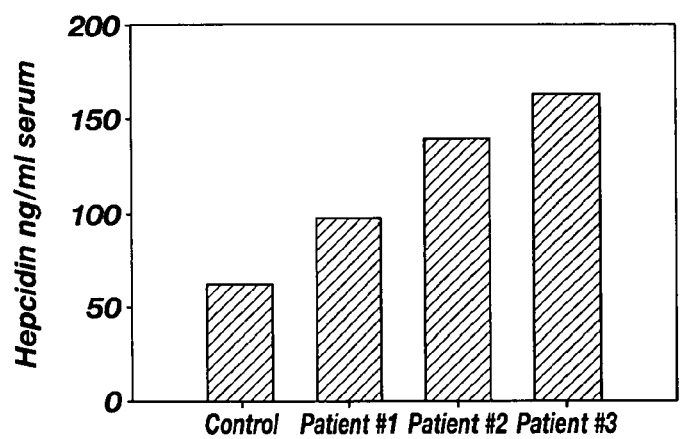
Figure 8E:
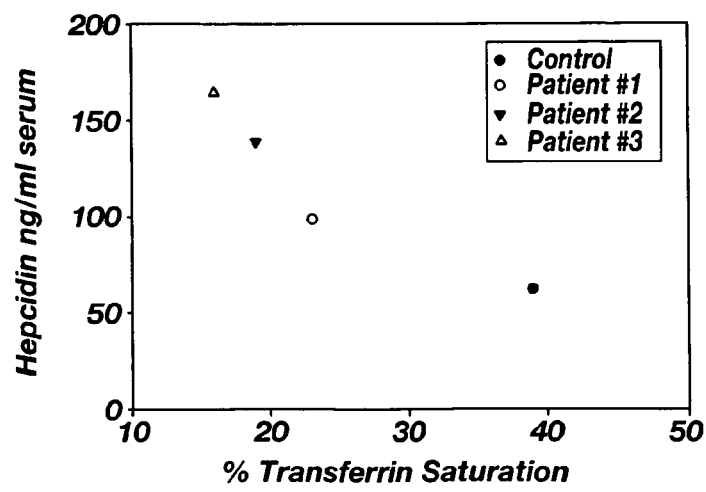

Sera of humans diagnosed as being infected with Lyme disease were tested, against sera of uninfected humans, to determine serum iron and transferrin saturation as parameters involved in iron metabolism as correlated to hepcidin (low hepcidin/high transferring saturation). Hepcidin levels from four patients were analyzed using the HBD-bead protocol described herein. Of the four patients analyzed, one was a non-infected human and three were humans infected with Lyme disease, but exhibiting different symptoms. Patient #1 (infected) was a 50-60 year old male presenting with flu-like symptoms and Jarisch Herxheimer reaction. Patient #2 (infected) was a 60-70 year old male presenting with disseminated Lyme disease and anaplasmosis (human granulocytic anaplasmosis [HGA]) characterized by fever, muscle aches, chills and muscle pain. Patient #3 (infected) was a 20-30 year old male presenting with meningitis. FIG. 8D illustrates the results of the hepcidin analyses in the four patients. Increase in hepcidin levels was determined to correlate with degree of disease severity, and showed an inverse correlation with serum iron levels and transferrin saturation. FIG. 8E shows inverse correlation of hepcidin levels and transferrin saturation. Table 4 below shows the comparative levels of serum iron and transferrin saturation of the patients.

TABLE 4

| Patient | Serum Iron (μg/dL) | Transferrin Saturation (%) |
|---|---|---|
| Control | 98 | 39 |
| #1 | 76 | 23 |
| #2 | 63 | 19 |
| #3 | 51 | 16 |

While this invention has been described in certain embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

Reference to known or conventional method steps, known methods or conventional methods is not an admission that any aspect, description or embodiment of the invention is disclosed, taught or suggested in the relevant art.

All references, including publications, patents, and patent applications, cited herein are hereby incorporated by reference to the same extent as if each reference were individually and specifically indicated to be incorporated by reference and were set forth in its entirety herein, including:

1. Ganz, T. & Nemeth, E. (2006) *Biochim Biophys Acta* 1763, 690-699;
2. Nemeth, E., Tuttle, M. S., Powelson, J., Vaughn, M. B., Donovan, A., Ward, D. M., Ganz, T., & Kaplan, J. (2004) *Science* 306, 2090-2093;
3. De Domenico, I., Ward, D. M., Langelier, C., Vaughn, M. B., Nemeth, E., Sundquist, W. I., Ganz, T., Musci, G., & Kaplan, J. (2007) *Mol Biol Cell.* 7:2569-2578;
4. De Domenico, I., Ward, D. M., Musci, G., & Kaplan, J. (2006) *Haematologica* 91, 92-95;
5. Zohn, I. E., De Domenico, I., Pollock, A., Ward, D. M., Goodman, J. F., Liang, X., Sanchez, A. J., Niswander, L., & Kaplan, J. (2007) *Blood.* 109:4174-4180;
6. De Domenico, I., Ward, D. M., Nemeth, E., Vaughn, M. B., Musci, G., Ganz, T., & Kaplan, J. (2005) *Proc Natl Acad Sci USA* 102, 8955-8960;
7. Nemeth, E., Preza, G. C., Jung, C. L., Kaplan, J., Waring, A. J., & Ganz, T. (2006) *Blood.* 107:328-333;
8. Hunter, H. N., Fulton, D. B., Ganz, T., & Vogel, H. J. (2002) *J Biol Chem* 277, 37597-37603;
9. Huang, F. W., Rubio-Aliaga, I., Kushner, J. P., Andrews, N. C., & Fleming, M. D. (2004) *Blood* 104, 2176-2177;
10. Lauth, X., Babon, J. J., Stannard, J. A., Singh, S., Nizet, V., Carlberg, J. M., Ostland, V. E., Pennington, M. W., Norton, R. S., & Westerman, M. E. (2005) *J Biol Chem* 280, 9272-9282;
11. Ganz, T. (1999) *Science* 286, 420-421;
12. Jacolot, S., Le Gac, G., Scotet, V., Quere, I., Mura, C., & Ferec, C. (2004) *Blood* 103, 2835-2840.

What is claimed is:

1. A protein-ligand conjugate suitable for use in a binding assay, which comprises: a hepcidin binding domain peptide covalently attached to a protein label or a solid support, wherein the hepcidin binding domain peptide consists of SEQ. ID. NO.: 1 and binds to hepcidin.

2. The protein-ligand conjugate of claim 1, wherein the hepcidin binding domain peptide is attached to a solid support.

3. The protein-ligand conjugate of claim 2, wherein the solid support is an agarose bead.

4. A protein-ligand conjugate suitable for use in a binding assay, which comprises: a hepcidin binding domain peptide covalently attached to a protein label or a solid support, wherein the hepcidin binding domain peptide comprises SEQ ID NO:1, wherein hydrophilic amino acids selected from the group consisting of arginine, aspartic acid, glutamic acid, glutamine, lysine, histidine, serine, threonine, and combinations thereof have been added at the amino and/or carboxyl terminal, and wherein the hepcidin binding domain peptide binds hepcidin.

5. The protein-ligand conjugate of claim 4, wherein the hydrophilic amino acids are arginines.

6. The protein-ligand conjugate of claim 4, wherein the hepcidin binding domain peptide consists of SEQ. ID. NO.:2.

7. The protein-ligand conjugate of claim 4, wherein the hepcidin binding domain peptide is a 24, 25, 30, 35 or 40 amino acid peptide.

8. The protein-ligand conjugate of claim 4, wherein the hepcidin binding domain peptide is a 24, 25 or 30 amino acid peptide.

* * * * *

UNITED STATES PATENT AND TRADEMARK OFFICE
CERTIFICATE OF CORRECTION

PATENT NO. : 8,530,619 B2  
APPLICATION NO. : 12/734061  
DATED : September 10, 2013  
INVENTOR(S) : Jerry Kaplan et al.

It is certified that error appears in the above-identified patent and that said Letters Patent is hereby corrected as shown below:

In the specification

COLUMN 1, LINES 18-21:

PLEASE DELETE "This invention was made with Government support under Grant DK 070947, awarded by the National Institutes of Health. The U.S. Government has certain rights to this invention."

AND INSERT --This invention was made with government support under grant numbers R01 DK070947 and P30 DK072437 awarded by National Institutes of Health. The government has certain rights in this invention.--

Signed and Sealed this
First Day of March, 2016

Michelle K. Lee
*Director of the United States Patent and Trademark Office*

SEQUENCE LISTING

<160> NUMBER OF SEQ ID NOS: 4

<210> SEQ ID NO 1
<211> LENGTH: 20
<212> TYPE: PRT
<213> ORGANISM: Homo sapiens

<400> SEQUENCE: 1

Phe Asp Cys Ile Thr Thr Gly Tyr Ala Tyr Thr Gln Gly Leu Ser Gly
1               5                   10                  15

Ser Ile Leu Ser
            20

<210> SEQ ID NO 2
<211> LENGTH: 24
<212> TYPE: PRT
<213> ORGANISM: Artificial Sequence
<220> FEATURE:
<223> OTHER INFORMATION: Hepcidin Binding Domain with amino acid
      additions

<400> SEQUENCE: 2

Arg Arg Phe Asp Cys Ile Thr Thr Gly Tyr Ala Tyr Thr Gln Gly Leu
1               5                   10                  15

Ser Gly Ser Ile Leu Ser Arg Arg
            20

<210> SEQ ID NO 3
<211> LENGTH: 24
<212> TYPE: PRT
<213> ORGANISM: Artificial Sequence
<220> FEATURE:
<223> OTHER INFORMATION: HBD Scramble

<400> SEQUENCE: 3

Arg Arg Ile Leu Ser Leu Phe Asp Ala Tyr Cys Thr Gly Thr Gln Ile
1               5                   10                  15

Thr Gly Ser Gly Ser Tyr Arg Arg
            20

<210> SEQ ID NO 4
<211> LENGTH: 24
<212> TYPE: PRT
<213> ORGANISM: Artificial Sequence
<220> FEATURE:
<223> OTHER INFORMATION: HBD Mutant

<400> SEQUENCE: 4

Arg Arg Phe Asp Tyr Ile Thr Thr Gly Tyr Ala Tyr Thr Gln Gly Leu
1               5                   10                  15

Ser Gly Ser Ile Leu Ser Arg Arg
            20